United States Patent [19]

Kroon et al.

[11] Patent Number: 5,364,978
[45] Date of Patent: Nov. 15, 1994

[54] PROCESS FOR REMOVAL OF TAR IN A PHENOL PREPARATION PROCESS

[75] Inventors: Johannes A. Kroon, Heerlen; Wim Buijs, Schinnen, both of Netherlands

[73] Assignee: D.S.M. N.V., Heerlen, Netherlands

[21] Appl. No.: 109,359

[22] Filed: Aug. 20, 1993

[30] Foreign Application Priority Data

Aug. 20, 1992 [NL] Netherlands .......................... 9201481

[51] Int. Cl.$^5$ ...................... C07C 37/00; C07C 37/68
[52] U.S. Cl. ................................... 568/801; 568/861; 568/800
[58] Field of Search ................ 568/801, 749, 761, 800

[56] References Cited

U.S. PATENT DOCUMENTS 3,130,235  4/1964  MacBeth ............................ 568/801
3,929,909  12/1975  van Die ................................ 568/801

FOREIGN PATENT DOCUMENTS 961287  6/1964  United Kingdom .

OTHER PUBLICATIONS

Chemical Abstract, vol. 101, No. 7, Aug. 13, 1984, Columbus, Ohio, Abstract No. 54705f.

*Primary Examiner*—Werren B. Lone
*Attorney, Agent, or Firm*—Cushman, Darby & Cushman

[57] ABSTRACT

The invention relates to a process for the preparation of a phenol by oxidative decarboxylation of benzoic acid in the presence of a copper-containing catalyst, wherein accumulation of tar components in the reactor is avoided by continuously removing a portion of the reaction mixture from the reactor and subjecting the removed portion to an extraction by contacting the removed portion with water and an auxiliary liquid, which auxiliary liquid is not miscible with water, wherein after extraction an aqueous liquid is obtained with benzoic acid and copper salts and an inorganic solution with tar components, wherein the aqueous solution is recycled to the reactor, the extraction being performed with 0.2 to 14 volume parts of auxiliary liquid per volume part of removed reaction mixture and with 0.5 to 10 volume parts of water per volume part of removed reaction mixture, the quantity of auxiliary liquid being so chosen that the resulting organic solution, containing auxiliary liquid, has a lower density than the aqueous solution, and the temperature during the extraction being higher than 80° C.

11 Claims, No Drawings

PROCESS FOR REMOVAL OF TAR IN A PHENOL PREPARATION PROCESS

The invention relates to a process for the preparation of a phenol, by oxidative decarboxylation of the corresponding benzoic acid in the presence of a copper-containing catalyst, wherein accumulation of tar components in the reactor is avoided by continuously removing a portion of the reaction mixture from the reactor and subjecting the removed portion to an extraction, by contacting the removed portion with water and an auxiliary liquid, which auxiliary liquid is not miscible with water, wherein after extraction an aqueous liquid is obtained with benzoic acid and copper salts and an organic solution with tar components, wherein the aqueous solution is recycled to the reactor.

The preparation of a phenol by an oxidative decarboxylation of the corresponding benzoic acid has been known for a long time already. Such a process is already described in NL-B-90684. According to NL-B-90684, the oxidation, the decarboxylation as well as the hydrolysis are carried out in the liquid phase, in a single process step, at a temperature of at least 200° C., preferably 230°–250° C.

In the said process many by-products are formed, mainly in the form of tar components.

Accumulation of these tar components in the reactor can be prevented by periodically or continuously withdrawing a portion of the liquid reaction mixture from the reactor and then effecting a separation between the tar components and the substances which are still valuable in the process, such as benzoic acid and copper salts and —if present—magnesium salts. The substances which are valuable in the process are subsequently returned to the reactor. The remaining solution containing the tar components will in general be burnt.

This separation of the tar components and substances which are valuable in the process is usually effected by extraction with an extraction agent which is a solvent for benzoic acid and copper and magnesium salts.

In general, water is used as extraction agent for this so-called tar extraction.

In practice it appears that such a separation by water extraction does not give satisfactory results because, among other things, rather much copper remains behind in the solution containing the tar components. Moreover, the ratio of the extraction selectivity toward the substances of value in the process and the extraction selectivity toward the tar components is unfavourable. In practice this means that if for instance a multistage countercurrent extraction is applied in order to achieve a certain recovery efficiency for these valuable substances, still a relatively large quantity of tar components is returned to the reactor with the aqueous extraction agent.

Extraction selectivity is the percentage of the quantity of a substance originally present in the reaction mixture to be extracted, which the extraction agent contains after one extraction step. The recovery efficiency is the percentage of the quantity of a substance originally present in the reaction mixture to be extracted which the extraction agent contains after completion of the extraction, which may comprise one or more extraction steps.

US-A-3130235 describes a process wherein the reaction mixture to be separated is extracted using an extraction agent and an auxiliary liquid which is immiscible with the extraction agent. The auxiliary liquid is chosen in such a way that the density of the auxiliarly liquid containing the tar particles is higher than the density of the extraction agent containing the desirable components, in order that any suspended tar particles that tend to settle, will accumulate at the bottom of the vessel. In this way, the extraction selectivity toward benzoic acid and copper and magnesium. salts is improved. It is not mentioned whether the extraction selectivity toward the tar components is (favourably) reduced. By preference, the lower halogenated aliphatic hydrocarbons, in particular perchloroethene, are used as auxiliary liquid. The extraction agent is preferably water with a water-miscible alcohol, in particular methanol.

A drawback of this known method is the use of substances foreign to the process, such as the halogenated aliphatic hydrocarbon and the alcohol. This requires additional purification steps in the process. Another drawback is that the organic solution containing the auxiliarly liquid, will contain halogenated hydrocarbons after the extraction, so that further processing of this solution without far-reaching environmental measures is virtually impossible.

The object of the invention is a simple separation by means of an extraction, using water as extraction agent, resulting in sufficient separation of benzoic acid, copper and any magnesium salts from the tar components.

This object is achieved in that the extraction is performed with 0.2 to 14 volume parts of auxiliary liquid per volume part of removed reaction mixture and with 0.5 to 10 volume parts of water per volume part of removed reaction mixture, the quantity of auxiliary liquid being so chosen that the resulting organic solution, containing the auxiliary liquid, has a lower density than the aqueous solution and that the temperature during the extraction is higher than 80° C.

When the extraction is performed in this way, appears that the water extracts both benzoic acid and the copper and magnesium salts very selectively. The tar components remain almost completely behind in the organic solution containing the auxiliary liquid and the extracted reaction mixture. This process is highly advantageous because it gives a good extraction selectivity toward the useful components without the use of process foreign or process hindering substances and without formation of solids which make additional process steps necessary.

The auxiliary liquids according to the invention are for instance non-halogenated hydrocarbons. The hydrocarbons in general for instance are non-substituted hydrocarbons having 5 to 10 carbon atoms. Examples of suitable auxiliary liquids are benzene, octane and toluene. These substances will not present special environmental problems when they are used in a process according to the invention. Particularly suitable are toluene and benzene, because these substances are non-process-foreign substances. Toluene is no process foreign substance in the process described in NL-B-90684, because the benzoic acid is prepared by oxidation of toluene. As a consequence, in an existing process there are in general provisions for the processing of toluene and the purification of toluene-containing flows. Further, in the distillative purification of phenol, toluene is in general used as auxiliary liquid substance in the separation of phenol and water. Benzene is not a process foreign substance because it is obtained as a by-product in the oxidative decarboxylation of benzoic acid.

Further, it has appeared that the process according to the invention results in a very efficient separation of a variety of tar components. Because a smaller amount of tar components is returned to the reactor at the same level of benzoic acid recovery, tar formation in the reactor is reduced.

It is a special advantage of the present invention that the copper concentration in the reaction zone can be increased, without causing an increase in tar formation compared with the state of the art. An increased copper concentration means a larger production of phenol per unit of reactorvolume. In this way the capacity and selectivity for phenol production of an existing plant can be increased.

In US-A-3130235, mentioned above, toluene and benzene are mentioned as possible auxiliary liquids for improvement of the extraction. In the same patent specification, however, the use of toluene and benzene is advised against. According to US-A-3130235, because of the low density of benzene and toluene, tar particles be suspended in the auxiliarly liquid will collect at the liquid interphase, thus complicating the problem of making a clean separation of the two liquid phases. Another reason for advising against the use of benzene and toluene is the greater tendency of these solvents to dissolve some of the desirable components of the reaction mixture, which results in an unfavourable loss of desirable reaction products and an inefficient extraction procedure.

In a process according to the invention the use of an auxiliary liquid appears to be advantageous owing to the employment of a countercurrent extraction column. A series of mixer-settlers will also give the desired results. The use of an auxiliary liquid offers the further advantage that the viscosity of the tar-component-containing organic solution is lowered, which makes it easier to treat this liquid. Another advantage is that after the extraction the aqueous solution and the organic solution de-mix easier.

GB-B-1297212 also describes a process in which a tar-component-containing reaction mixture in the phenol preparation process is extracted with water (acidified, if required) in the presence of toluene.

According to GB-B-1297212 the extraction with water is carried out in such a way that only the copper and magnesium salts are extracted and that the benzoic acid remains behind in the organic solution. This is achieved either by extracting with a lot of water, in which case dissolution of benzoic acid in the aqueous solution is prevented by raising the degree of acidity of the aqueous solution, or by extracting with a small quantity of water, so that the metal salts that are present are fully precipitated and only little benzoic acid can dissolve. The benzoic acid is then recovered by distilling it out of the tar-component-containing organic solution. Next, the metal salts and the benzoic acid are returned to the reactor. In this way, it is said, in particular less copper remains behind in the organic solution, so that less copper catalyst is lost. Drawbacks of this process are the large number of process steps, including the invariably difficult solids handling steps, and the use of an acidified extraction agent.

JP-A-59029626 also describes a process in which toluene is supplied to a tar-component-containing reaction mixture, in the phenol production process, before this mixture is extracted with water. In that process the extraction with water is effected with the molar ratio between water and the total amount of catalytically active components (e.g. Cu and Mg) lying between 10:1 and 100:1, at a temperature between 20° and 180° C. and a pressure between 0.1 and 1 MPa. Characteristic of that invention is that the catalytically active components precipitate in the aqueous solution. A drawback of the process is that for further treatment of this solid phase the difficult process steps such as filtration and crystallization are required. Another drawback of this known process is that after the extraction so much benzoic acid still remains behind in the organic solution that an additional process step is required to remove the benzoic acid and return it to the reactor. In the process according to the present invention this additional process step is not required.

The preparation of phenol by means of an oxidative decarboxylation of benzoic acid is carried out with a copper-containing catalyst. The copper concentration in the (separated) reaction mixture will in general be between 0.5 and 10 wt. % relative to the total mixture. By preference, the copper concentration will be between 1 and 5 wt. %. Besides copper the catalyst will in general contain a co-catalyst. Such a co-catalyst is preferably an element from groups V, VI, VII or VIII, or from the group of lanthanides and actinides, of the Periodic System of the Elements. In addition, promotors can be used; in particular (earth) alkaline metals, such as magnesium or lithium, are suitable as such. By preference, the concentration of these co-catalysts and/or these promotors is between 1 and 10 wt. %.

The composition of the reaction mixture that is withdrawn from the phenol preparation reactor depends on, among other things, the catalyst system used, the concentrations of the catalyst and the starting materials, and the process conditions. The phenol concentration in the separated reaction mixture can vary from almost nil to 6 wt. %.

The amount of tar components in the separated reaction mixture will in general be between 1 and 30 wt. %, in particular between 4 and 30 wt. %.

Besides phenol and tar components a quantity of diphenyl ether and phenyl benzoate is formed, in general amounting to a total of between 1 and 5 wt. %. The quantity of non-converted benzoic acid in the form of free benzoic acid and metal benzoates constitutes the remaining portion of the mixture. The metal benzoates are benzoates of the copper and the co-catalyst metals mentioned above.

The pressure and temperature at which the extraction is effected are in general chosen such that the water-/auxiliary liquid/reaction mixture system does not boil. In general the pressure is between 0.1 and 6 MPa and the temperature between 80° and 250° C. Preferably, the pressure is between 0.2 and 4 MPa and the temperature between 100° and 220° C., in particular between 120° and 160° C. An additional advantage of working at a temperature higher than 80° C. is that no substantial additional cooling is required for the reaction mixture leaving the reactor. The temperature decrease can be achieved simply by effecting the extraction with auxiliary liquid and/or water at room temperature.

The volume ratio between auxiliary liquid and the removed reaction mixture is in general between 0.2 and 10; preferably, it will be between 0.5 and 5 because a quantity of auxiliary liquid, in particular a quantity of toluene, larger than 5 times the volume of the removed reaction mixture is economically less attractive. More in particular, a ratio of about 1 appears to give very good results. The volume ratio between water and removed reaction mixture is in general between 0.5 and 10, preferably between 0.8 and 2.5, in particular around 1.5.

The extraction is preferably carried out in several steps, with the organic phase and the water phase in countercurrent. Such a process could be carried out for instance in a series of mixer-settlers. In this case it would be possible, instead of the above-mentioned countercurrent principle, to use clean water in each separation. The extraction can also be carried out well in an extraction column. Preferably, such an extraction column will be a rotating disk column or a column of similar type. The required number of extraction steps can easily be determined by one skilled in the art and will as a rule be between 4 and 12.

The removed reaction mixture, the auxiliary liquid and the water can be contacted with each other simultaneously. It is also possible first to contact the reaction mixture with the auxiliarly liquid and subsequently with the water.

The auxiliary liquid in the organic solution will in general be recovered after the extraction. The auxiliary liquid according to the invention can be separated from the organic solution in a simple manner, for instance by means of distillation. If desired, the auxiliary liquid can be re-used in the process according to the invention. Any useful components which are separated from the organic solution together with the auxiliary liquid are returned to the process in this way. The organic phase will in general be burnt after removal of the auxiliary liquid.

The invention will be elucidated further in the following examples, without being restricted thereto.

EXAMPLE I

An autoclave was filled with 560 ml toluene, 480 ml water and 380 ml reaction mixture of the following composition:

| | |
|---|---|
| phenol: | 1.0 wt. % |
| total benzoic acid/benzoate: | 67.8 wt. % |
| magnesium: | 3.5 wt. % |
| copper: | 1.0 wt. % |
| tar components: | 25.0 wt. % |
| water: | 1.7 wt. % |

At a temperature of 140° C. and a pressure of 1MPa, stirring was applied for 15 minutes at 1470 rpm. The stirrer was stopped and after 6 minutes it appeared that two separate phases had formed, the upper phase being the organic solution and the lower phase the aqueous solution. The total benzoate content was determined by HPLC. (High Pressure Liquid Chromatography) analysis. The compositions of the upper and the lower phase were:

| | organic solution (wt. %) | aqueous solution (wt. %) |
|---|---|---|
| phenol: | 0.4 | 0.2 |
| total benzoic acid/benzoate: | 10.8 | 29.0 |
| magnesium: | 0.1 | 2.0 |
| copper: | 0.1 | 0.4 |
| tar components: | 13 | 1 |
| toluene: | 64 | 1 |
| water: | 11 | 67 |

The extraction selectivity toward benzoate was 72%, toward the tar components 7%, toward copper 75% and toward magnesium 95%.

EXAMPLE II

Example I was repeated. The organic solution was separated from the aqueous solution. Next, 480 ml 'clean' water was added to the organic solution. Under the same conditions as in Example I the mixture was mixed and analyzed. The extraction efficiency after these two extraction steps was 82% for benzoate, 8% for the tar components, 87% for copper and 100% for magnesium.

Experiment A

An autoclave was filled with 600 ml water and 500 ml reaction mixture of the same composition as the reaction mixture used in Example I. At a temperature of 140° C. and a pressure of 1 MPa, stirring was applied for 15 minutes at 1470 rpm. The stirrer was stopped and after 15 minutes it appeared that two separate phases had formed, the upper phase being the aqueous solution and the lower phase the organic solution. The total benzoate content was determined by HPLC. analysis. The compositions of the upper and the lower phase were:

| | organic solution (wt. %) | aqueous solution (wt. %) |
|---|---|---|
| phenol: | 0.6 | 0.4 |
| total benzoic acid/benzoate: | 25.6 | 30.6 |
| magnesium: | 0.3 | 1.6 |
| copper: | 1.3 | 0.4 |
| tar components: | 66 | 9 |
| water: | 6 | 58 |

The extraction selectivity toward benzoate was 94%, toward the tar components 74%, toward copper 82% and toward magnesium 99%.

We claim:
1. Process for preparing a phenol comprising the steps of:
   conducting an oxidative decarboxylation of the corresponding benzoic acid in the presence of a copper-containing catalyst in a reactor whereby a reaction mixture is obtained in the reactor; is avoided by
   continuously removing a portion of the reaction mixture from the reactor;
   subjecting the removed portion to an extraction by contacting the removed portion with water and, as an auxiliary liquid, a non-halogenated hydrocarbon compound which is not miscible with water, wherein after extraction an aqueous liquid is obtained containing benzoic acid and copper salts and an organic solution is obtained containing tar components, wherein accumulation of tar in the reactor is avoided, and
   recycling the aqueous solution to the reactor, wherein the extraction is performed with 0.2 to 14 volume parts of auxiliary liquid per volume part of removed reaction mixture and with 0.5 to 10 volume parts of water per volume part of removed reaction mixture, the quantity of auxiliary liquid being so chosen that the resulting organic solution, containing auxiliary liquid, has a lower density then the aqueous solution and that the temperature during the extraction is higher than 80°.

2. Process according to claim 1, characterized in that the hydrocarbon compound is toluene.

3. Process according to claim 1, characterized in that the removed reaction mixture is mixed with 0.5 to 5 volume parts of auxiliary liquid per volume part of removed reaction mixture.

4. Process according to claim 1, characterized in that 0.8 to 2.5 volume parts of water per volume part of removed reaction mixture are used for the extraction.

5. Process according to claim 1, characterized in that the extraction is carried out in two or more extraction steps.

6. Process according to claim 1, characterized in that the auxiliary liquid is recovered from the organic solution after the extraction and returned to the process and that the remaining solution with tar components is drawn off.

7. Process according to claim 1, characterized in that the extraction is carried out at a pressure between 0.2 and 4 MPa and a temperature between 100° and 220° C., pressure and temperature being chosen such that the water/auxiliarly liquid/reaction mixture does not boil.

8. Process according to claim 1, characterized in that the removed portion of reaction mixture is first contacted with the auxiliary liquid and subsequently with water.

9. A process for preparing a phenol comprising the steps of:
   conducting an oxidative decarboxylation of the corresponding benzoic acid in the presence of a copper-containing catalyst in a reactor, wherein the copper concentration ranges are from between 0.5 and 10 wt. % relative to the total reaction mixture;
   continuously removing a portion of said reaction mixture from the reactor and subjecting said removed portion to an extraction by contacting said removed portion with water and a water-immiscible auxiliary liquid comprising a non-halogenated hydrocarbon compound, wherein said auxiliary liquid is present in an amount of 0.2 to 14 volume parts per volume part of said removed reaction mixture and said water is used in an amount of 0.5 to 10 volume parts of water per volume part of said removed reaction mixture, whereby an organic solution, containing said auxiliary liquid, is obtained, said resulting organic solution having a lower density than said aqueous solution which is obtained following said extraction, said extraction being conducted at a temperature greater than 80° C., whereby after said extraction an organic solution containing tar components is obtained and aqueous solution is obtained which contains benzoic acid and copper salts; and
   recycling said aqueous solution to said reactor.

10. Process according to claim 1, wherein said extraction is performed in a countercurrent extraction column.

11. Process according to claim 9, wherein said extraction is performed in a countercurrent extraction column.

* * * * *